United States Patent [19]

Hashimoto et al.

[11] Patent Number: 5,037,958

[45] Date of Patent: Aug. 6, 1991

[54] IMMUNOSUPPRESSIVE FACTOR

[75] Inventors: Yoshiyuki Hashimoto, Sendai; Kenji Chiba, Tokyo; Hirotsugu Komatsu, Tokyo; Takeki Okumoto, Tokyo, all of Japan

[73] Assignee: Yoshitomi Pharmaceutical Industries, Ltd., Osaka, Japan

[21] Appl. No.: 146,167

[22] PCT Filed: Apr. 27, 1987

[86] PCT No.: PCT/JP87/00268

§ 371 Date: Dec. 11, 1987

§ 102(e) Date: Dec. 11, 1987

[87] PCT Pub. No.: WO87/06591

PCT Pub. Date: Nov. 5, 1987

[30] Foreign Application Priority Data

May 2, 1986 [JP] Japan .................. 61-102498

[51] Int. Cl.$^5$ .................. C07K 3/00; C07K 13/00; C07K 15/04; C07K 15/06
[52] U.S. Cl. ................... 530/350; 530/351; 530/827; 530/829
[58] Field of Search ............. 530/350, 351, 827, 300, 530/829

[56] References Cited

U.S. PATENT DOCUMENTS 4,613,459  9/1986  Cantor et al. ............ 530/351
4,785,077  11/1988  Kornbluth et al. ........ 530/351

FOREIGN PATENT DOCUMENTS 88320  5/1983  Japan .
138395  8/1983  Japan .
116224  4/1984  Japan .
183750  6/1987  Japan .
4421  10/1985  PCT Int'l Appl. .

OTHER PUBLICATIONS

Chem. Abstracts, vol. 102, 1985, 111180c, Chiba et al.
Chem. Abstracts, vol. 102, 1985, 11118id, Chiba et al.
Chem. Abstracts, vol. 103, 47752, Chiba et al.
Federation Proceedings, vol. 44, No. 3, 1985, p. 511, abstract No. 941, N. Everett et al. (Abstract).
Schnaper et al., The Journal of Immunology, vol. 132, pp. 2429-2435 (1984).
Greene et al., op.cit., vol. 126, pp. 1185-1191 (1981).
Fleisher et al., op.cit., vol. 126, pp. 1192-1197 (1981).
Lau et al., op.cit., vol. 134, pp. 3155-3162 (1985).
Fontana et al., op.cit., vol. 132, pp. 1837-1844 (1984).
Hersey et al., op.cit., vol. 131, pp. 2837-2842 (1983).
Santoli et al., J. Exp. Med., vol. 163, pp. 18-40 (Jan. 1986).

Primary Examiner—Nathan M. Nutter
Attorney, Agent, or Firm—Wenderoth, Lind & Ponack

[57] ABSTRACT

A new immunosuppressive factor derived from human T cell leukemia cells characterized by the following properties:
(1) molecular weight: 45,000 to 65,000 daltons and 150,000 to 200,000 daltons by gel filtration, and approximately 31,000 daltons by SDS-polyacrylamide gel electrophoresis;
(2) isoelectric point: 4.6 to 4.8;
(3) being elutable at a concentration of 0.31 to 0.32 M sodium chloride by FPLC-Mono Q anion exchange chromatography;
(4) not adsorbable to immobilized concanavalin A Sepharose or blue Sepharose;
(5) resistant to deoxyribonuclease, ribonuclease, papin and periodic acid but sensititive to trypsin, α-chymotrypsin or pronase;
(6) stable at pH 2 to 10;
(7) stable for a long time at 4° C. but partially inactivated by heat treatment at 56° C. or 90° C. for 30 minutes;
(8) not inhibitable by 2-mercaptoethanol, levamisole, N-acetyl-D-glucosamine, N-acetyl-D-galactosamine, α-methyl-D-mannoside, L-arginine or L-ornithine;
(9) suppressing production of antibody;
(10) suppressing blastogeneis of lymphocytes;
(11) suppressing cell proliferation; and
(12) having structural amino acid and specific contents thereof.

This immunosuppressive factor has an excellent immunosuppressing effect and is useful as medicine or reagent.

1 Claim, 9 Drawing Sheets

IMMUNOSUPPRESSIVE FACTOR

FIELD OF THE INVENTION

The present invention relates to a new immunosuppressive factor deriving from human cells

BACKGROUND OF THE INVENTION

It is known that various immunomodulatory factors (also referred to as lymphokines) are produced by human T cells, and some of these immunomodulatory factors are present as factors possessing immunosuppressive activity by which immune response is attenuated.

For example, Schnaper et al. reported that a factor possessing suppressive activity on polyclonal antibody production by human B cells stimulated with pokeweed mitogen (soluble immune response suppressor: SIRS) is produced as an immunosuppressive factor derived from human T cells in culture supernatant by stimulated human spleen cells (specifically OKT 8 positive suppressor T cells) with concanavalin A [J. Immunol., vol. 132, p. 2429(1984)]. The factor SIRS has a molecular weight of 110,000 to 150,000; it is inactivated by pH 3 treatment; it is activated by oxidizing agents such as hydrogen peroxide; it is inactivated by reducing agents such as 2-mercaptoethanol.

Greene et al. reported that a factor possessing suppressive activity on blastogenesis of human T cell by phytohemagglutinin stimulation (soluble immune suppressor supernatant of T cell proliferation SISS-T) and another factor which suppresses polyclonal antibody production by human B cells stimulated with pokeweed mitogen (soluble immune suppressor supernatant of B cell immunoglobulin production: SISS-B) are produced from human peripheral blood lymphocytes stimulated by concanavalin A. It was demonstrated that the factor SISS-T has a molecular weight of 30,000 to 45,000, whose activity is inhibited by addition of N-acetyl-D-glucosamine, and the factor SISS-B has a molecular weight of 60,000 to 80,000, whose activity is inhibited by addition of L-rhamnose [J. Immunol., vol. 126, p. 1185 (1981)].

In addition, it was reported that factors possessing suppressive activities on immune reaction are produced from various T cell lines such as T cell leukemia cells, as well as normal human T cells. For example, as a factor derived from human leukemia cells, Catharine et al. reported that a factor which activates suppressor T cells (suppressor-activating factor: SAF), is produced by 6-thioguanine-resistant human T cell leukemia cell CCRF-CEM [J. Immunol., vol. 134, p. 3155 (1985)-. Santoli et al. found that a factor which suppresses proliferation of human leukemia cells themselves (T leukemia-derived suppressor lymphokine: TLSL) is produced from human T cell leukemia cells such as CCRF-CEM and HUT-78 [J. Exp. Med., vol. 163, p. 18 (1986)]. Moreover, Hersey et al. found that factors which have a molecular weight of 44,000 or 7,000 and which specifically suppress production of interleukin 2 by T cells are produced by melanoma cells LJ. Immunol., vol. 131, p. 2837 (1983)-, and it was reported by Fontana et al. that a factor which has a molecular weight of 97,000 and which suppresses proliferation of interleukin 2dependent T cells is produced by human neuroglioblastoma cells [J. Immunol., vol. 132, p. 1837 (1984)].

In addition, Hashimoto et al. found that, when human peripheral blood lymphocytes are stimulated with concanavalin A, a factor which suppresses DNA synthesis in various cells (stimulated T cell derived inhibitory factor for cellular DNA synthesis: STIF) is produced. It was demonstrated that the factor STIF is a factor of protein nature having a molecular weight of 45,000 to 65,000 and an isoelectric point of 4.5 to 5.5, and it is produced by OKT 8 positive suppressor T cells.

DISCLOSURE OF THE INVENTION

As stated above, there are many reports on various immunosuppressive factors derived from activated human T cells. In almost all cases, however, these factors have not been isolated or purified in sufficient amounts to know their molecular properties, amino acid compositions, amino acid sequences, etc., and in addition, the action mechanisms of these factors yet remain to be completely clarified. Therefore, investigations are being made in search of even more effective bioactive factors in the relevant field.

Taking note of these conditions, the present inventors made intensive investigations; as a result, the inventors found that a new immunosuppressive factor is produced at high concentration from human T cells, and completed the invention based on this finding.

Accordingly, the present invention relates to a new immunosuppressive factor derived from human T cell lines and characterized by the following properties:

(1) molecular weight: 45,000 to 65,000 daltons and 150,000 to 200,000 daltons by gel filtration, and approximately 31,000 daltons by SDS-polyacrylamide gel electrophoresis;
(2) isoelectric point: 4.6 to 4.8;
(3) being elutable at a concentration of 0.31 to 0.32 M sodium chloride by FPLC-Mono Q anion exchange chromatography;
(4) not adsorbable to immobilized concanavalin A Sepharose or blue Sepharose;
(5) resistant to deoxyribonuclease, ribonuclease, papain and periodic acid but sensitive to trypsin, α-chymotrypsin or pronase;
(6) stable at pH 2 to 10;
(7) stable for a long time at 4° C, but partially inactivated by heat treatment at 56° C or 90° C for 30 minutes;
(8) not inhibitable by 2-mercaptoethanol, levamisole, N-acetyl-D-glucosamine, N-acetyl-D-galactosamine, α-methyl-D-mannoside, L-arginine or L-ornithine;
(9) suppressing production of antibody;
(10) suppressing blastogenesis of lymphocytes;
(11) suppressing cell proliferation; and
(12) having structural amino acids whose contents (mol %) are asparagine (including aspartic acid), 9.0 mol %; threonine, 4.7 mol %; serine, 8.5 mol %; glutamine (including glutamic acid), 13.1 mol %; glycine, 16.9 mol %; alanine, 10.4 mol %; valine, 5.2 mol %; methionine, 1.1 mol %; isoleucine, 3.5 mol %; leucine, 7.3 mol %; tyrosine, 2.3 mol %; phenylalanine, 4.2 mol %; lysine, 5.8 mol %; histidine, 2.2 mol %; arginine, 3.7 mol %; proline, 2.3 mol %; ½ cystine, <1 mol %; and tryptophan, <1 mol %.

BRIEF EXPLANATIOON OF THE DRAWINGS

DETAILED DESCRIPTION OF THE INVENTION

Figure 1:
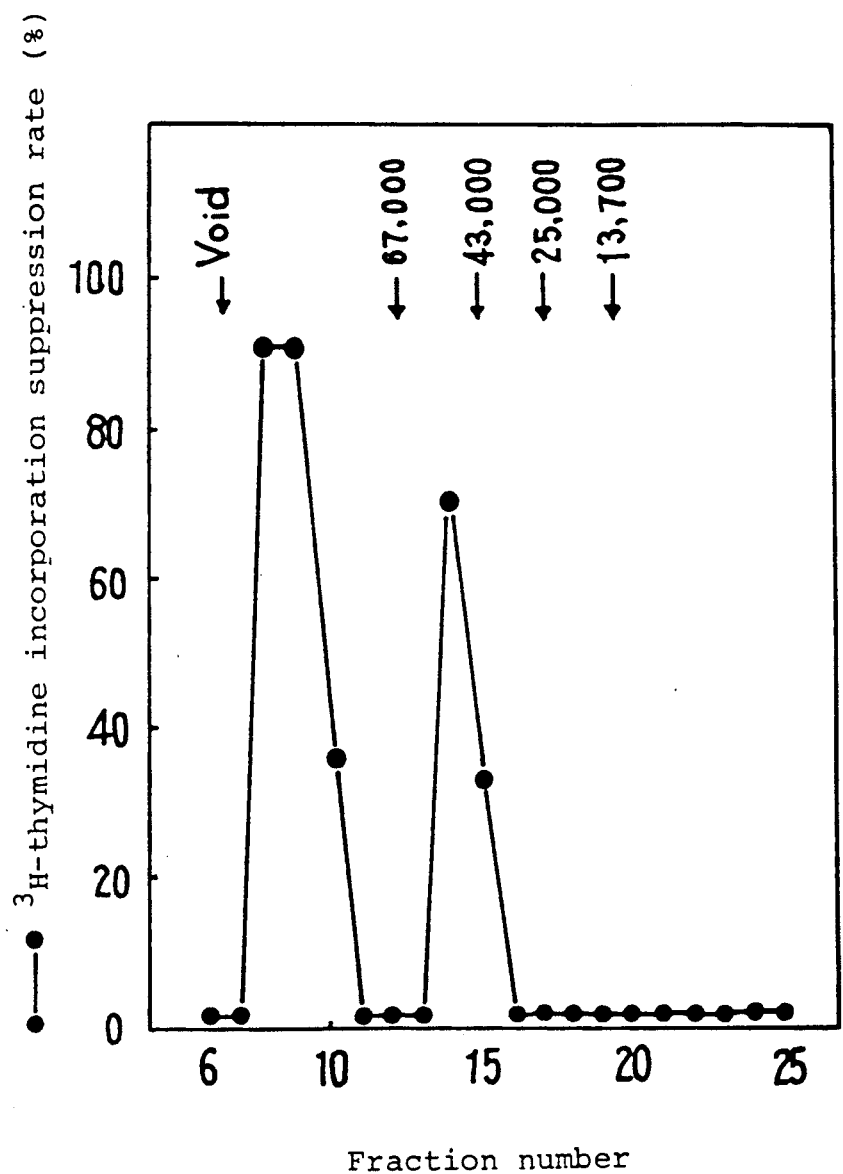
FIG. 1 shows the elution pattern in gel filtration using the FPLC-Superose 12 column.

As producer cells for the immunosuppressive factor of the present invention, human T cell lines in particular human T cell leukemia cells can be used. Specifically, established human T cell-mediated leukemia cells which are not infected with mycoplasma, for example, MOLT 4, MOLT 3, CCRF-HSB2, CCRF-CEM available from the American Type Culture Collection (ATCC) etc. can be used.

The immunosuppressive factor of the present invention is produced by these cells growing in vitro or in vivo with or without mitogen stimulation. Any mitogen can be used, as long as it is capable of inducing the immunosuppressive factor of the present invention. As examples of such mitogens, mention may be made of lectins such as concanavalin A (Con A), phytohemagglutinin (pHA) and pokeweed mitogen (PWM); phorbol esters such as 12-0-tetradecanoylphorbol-13-acetate, phorbol-12,13-didecanoate and phorbol-12,13-dibenzoate; and alloantigens. These can be used alone or in combination.

Methods used to produce the immunosuppressive factor of the present invention include the method of cultivation in vitro in which various animal cells are allowed to grow in an ordinary medium which contains or does not contain serums of various animals (preferably fetal calf serum) or heat-inactivated products thereof and on which said animal cells can grow (e.g., RPMI 1640 medium, Eagle MEM medium, Dulbecco's modified Eagle MEM medium) and the method of growing in vivo in which the above-mentioned cells are transplanted to a warm-blooded animal to which nude mouse or nude rat tumor cells can be transplanted, and they are allowed to grow in the body thereof. The immunosuppressive factor of the present invention can be substantially limitlessly obtained from culture supernatant of these cells, ascites, and so on.

The immunosuppressive factor of the present invention thus produced can be isolated and purified by employing in any combination routine methods generally used for protein separation such as salting-out, centrifugation, dialysis, gel filtration chromatography, ion exchange chromatography, affinity chromatography, reverse-phase chromatography, hydrophobic chromatography, chromatofocusing, electrophoresis, ultrafiltration and lyophilization.

A production, isolation and purification method preferable for the present invention is as follows: Human T cell leukemia cells, with or without mitogen stimulation, are cultured in a medium in which animal cells can grow. The obtained culture supernatant is concentrated by means of ultrafiltration or salting-out, whereafter gel filtration is carried out using a carrier which is suitable for separation of substances having a molecular weight of 10,000 to 250,000. The active fraction containing the immunosuppressive factor of the present invention, thus obtained can be purified up to a single band by carrying out elution by anion exchange chromatography using a carrier having an anion exchanging group such as quarternary ammonium group or diethylaminoethyl group with, for example, a salt linear gradient sodium chloride solution, and, after migration by an electrophoresis technique such as polyacrylamide gel electrophoresis or SDS-polyacrylamide gel electrophoresis, cutting out the gel, and subjecting it to further elution.

Purification can also be achieved by preparative isoelectric focusing or chromatofocusing. The immunosuppressive factor of the present invention can be obtained as a fraction of pH 4.6 to 4.8 by preparative isoelectric focusing and in addition it can also be purified by affinity chromatography using immobilized concanavalin A Sepharose or blue Sepharose.

The immunosuppressive factor of the present invention thus purified is preferably stored in the lyophilized state and so on.

Having properties as shown above, the immunosuppressive factor of the present invention is a novel factor which is different from conventional human cell-derived immunosuppressive factors.

In activity determination of immunosuppressive factors, various immune reactions using mouse, rat or human lymphocytes can be used. For example, lymphocyte blast formation using a mitogen such as concanavalin A, phytohemagglutinin or pokeweed mitogen [Adler, W. H. et al., J. Exp. Med., vol. 131, p. 1049 (1970)], allogenic mixed lymphocyte reaction (allogenic MLR) Dutton, R. W. et al., J. Exp. Med., vol. 122, p. 759 (1965)], antibody production by lymphocytes, in particular by B cells, etc. can be used as an index. That is, it is known that, when lymphocytes are stimulated with mitogen or antigen such as major histocompatibility antigen, what is called lymphocyte blastogenic transformation is induced, in which DNA synthesis in lymphocytes, in particular in T cells, is promoted so that cell division is initiated. As a determination method for this lymphocyte blastogenic transformation, the method in which $^3$H-thymidine incorporation into cells is measured as an index of DNA synthesis and cell division is generally used. The activities of immunosuppressive factors can therefore be determined as suppressive activities on increase in $^3$H-thymidine incorporation due to various lymphocyte blastogenic transformation reactions (mitogen response, allogenic MLR, etc.).

The activities can also be evaluated as suppressive activities on antibody (immunoglobulins A, D, E, G, M, etc.) production by B cells stimulated and activated by antigen or mitogen.

On the other hand, it has recently been demonstrated that T cell proliferation due to mitogen reaction, allogenic MLR, etc. is mediated by T cell-derived soluble factors (lymphokines) such as interleukin 2 [Morgan, R. A. et al., Science, vol. 193, p. 1007 (1976)- A large number of such factors which modulate immune reaction have been discovered, such as interleukin 1, 2, 3 or 4, colony stimulating factors, interferon Y or lymphotoxin. It is therefore possible to evaluate the activities of immunosuppressive factors also as suppressive activities on blastogenesis or functions of lymphocytes induced by these factors.

As obvious from the experimental examples shown later, the immunosuppressive factor of the present invention exhibited excellent immunosuppressive activities in these evaluation systems.

For these reasons, the immunosuppressive factor of the present invention can not only be used to suppress transplantation rejection in patients subjected to xeno- or allotransplantation of the bone marrow, kidney, heart, etc. but also applied to prevention or treatment of autoimmune diseases such as systemic lupus erythematodes and rheumatoid arthritis and diseases based on allergy or abnormality of lymphocyte proliferation. In addition, this factor can also be widely used as reagents etc. in the fields of medicine and pharmacology.

When used as medicine, the immunosuppressive factor of the present invention may be prepared in accordance with ordinary preparation techniques; for example, its bulk may be mixed with carrier, excipient, diluent, etc. to provide in the form of a powder, tablet, capsule, injection, and so on. The factor can also be used in a lyophilized state.

The present invention will now be described in more detail according to the following working examples and experimental examples, but the present invention is never limited by these examples.

As in the following working examples etc., the immunosuppressive factor of the present invention was searched for by using $^3$H-thymidine incorporation suppression in rat bone marrow cells as an index. The procedure was as follows: Activity determination: $^3$H-thymidine incorporation suppression in rat bone marrow cells Using a 96-well microtestplate (made by Corning) as a cultivation vessel, 0.1 ml of a rat bone marrow cell suspension ($5 \times 10^6$ cells/ml) prepared using an RPMI 1640 medium containing 10% heat-inactivated fetal calf serum and 0.1 ml of a dilute sample were mixed together, and this mixture was cultured at 37° C. for 12 hours under an atmosphere containing 5% carbon dioxide gas in air. $^3$H-thymidine (specific activity, 5 Ci/mmol, produced by Amarsham) was then added to a concentration of 0.5 µCi/well, and cultivation was continued for 4 more hours, whereafter cells were collected onto a glass fiber filter by means of a cell harvester. The radioactivity incorporated into the cells was determined by means of a liquid scintillation counter using a toluene scintillator; percent suppression of 3H-thymidine incorporation was calculated with the following formula, and it is expressed as an index for the activities of the present immunosuppressive factor.

Suppression (%) =

$$\left(1 - \frac{cpm. \text{ in the presence of a test sample}}{cpm. \text{ in the absence of the test sample}}\right) \times 100$$

Titers can be expressed in unit (U) by plotting sample dilution rates and suppression rates on normal probability paper etc. to determine the dilution rate at which a $^3$H-thymidine incorporation suppression rate of 50% is obtained.

EXAMPLE 1

Each of human T cell leukemia cell line MOLT 4, MOLT 3, CCRF-HSB2 and CCRF-CEM and human B lymphoblastoid cell line, RPMI 1788 was cultured in RPMI 1640 medium containing 10% heat-inactivated fetal calf serum, 60 µg/ml of kanamycin sulfate, 10 mM N-2-hydroxyethylpiperazine-N'-2-ethansulfonic acid, 2 mM L-glutamine and 0.1% sodium hydrogencarbonate. The immunosuppressive activity of the culture supernatants was assayed for the inhibitory activity against $^3$H-thymidine incorporation into rat bone marrow cells as an index.

As a result, a strong immunosuppressive activity was detected in the culture supernatants of MOLT 4 and CCRF-HSB2 cells and a weak immunosuppressive activity was detected in the culture supernatant of CCRF-CEM cells, but no activity was detectable in human B lymphoblastoid cell line, RPMI 1788 which is known as a lymphotoxin-producing cell line. All of human cultured cell lines which were employed in this Example were not infected with mycoplasma.

Highly producing clones of the immunosuppressive factor were obtained by cloning of MOLT 4 or CCRF-HSB2 cells according to a limiting dilution method. Among them, MOLT 4 clone 1E9 could be obtained as a characteristically high-producing clone and the clone was also employed in the following Examples.

The production conditions of the immunosuppressive factor were examined by using MOLT 4 clone 1E9. As a result, the production of the factor reached the maximal level after 72 hours when unstimulated MOLT 4 clone 1E9 cells were cultured at $10^6$ cells/ml in a serum free RPMI 1640 medium under an atmosphere of 5% $CO^2$ in air at 37° C.

When MOLT 4 clone 1E9 cells were stimulated with 10 µg/ml of concanavalin A (Sigma), the production of the immunosuppressive factor reached the maximal level at 12 hours after stimulation.

EXAMPLE 2

Human T cell leukemia cell line, MOLT 4 or its clone MOLT 4 clone 1E9 cells were cultured at $10^6$ cells/ml in a serum free RPMI 1640 medium for 72 hours at 37° C. under an atmosphere of 5% $CO_2$ in air. Then, the culture supernatants were harvested by centrifugation to remove cells and concentrated by ultrafiltration with Follow Fiber (Amicon) and the like to about 1/100 of the original volume. Thus obtained concentrated culture supernatants (hereinafter referred to as "concentrated culture supernatant") were subjected to purification after the immunosuppressive activity in the supernatant was assayed with rat bone marrow cells.

The concentrated culture supernatants were fractionated by gel filtration on a Sephacryl S-200 column (1.4×90 cm) or a FPLC-Superose 12 column (HR10/30) (Pharmacia) by eluting phosphate-buffered saline solution (pH 7.4). The chromatogram was calibrated with standard proteins (Pharmacia: ribonuclease A, chymotrypsinogen A, ovalbumin and bovine serum albumin) and the molecular weight was determined in respect of each fraction obtained by gel filtration.

As shown in FIG. 1, according to the assay for the immunosuppressive activity with rat bone mallow cells, the peaks of activity of the immunosuppressive factor of the present invention were detected in the fractions eluted between ovalbumin and bovine serum albumin and the two fractions eluted before bovine serum albumin, and the molecular weight was found to be 45,000–65,000 and 150,000–200,000.

Figure 2:
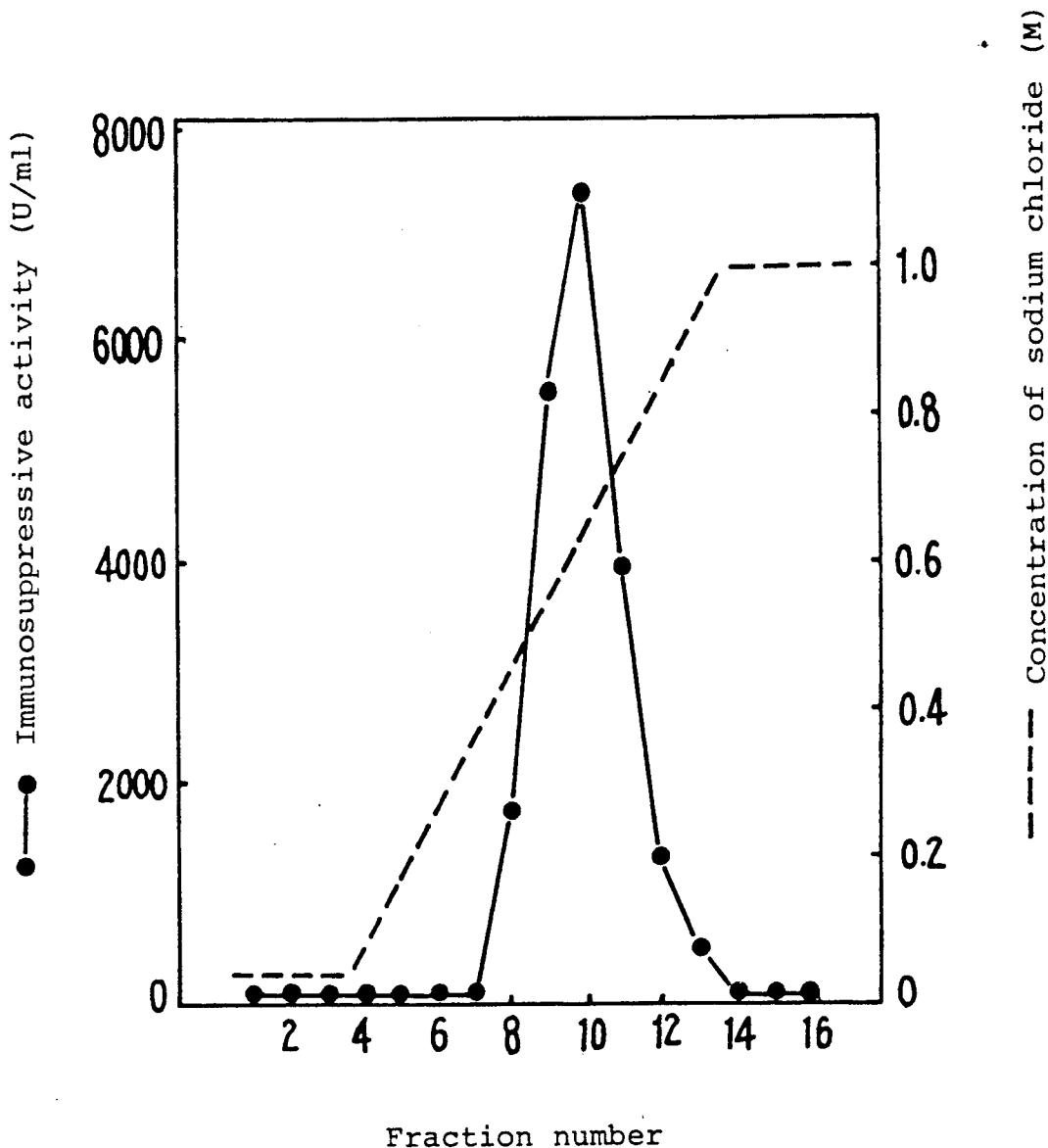
FIG. 2 shows the elution pattern in anion exchange chromatography using the FPLC-Mono Q column with a linear gradient of 0 to 1 M sodium chloride.

After the active fractions obtained by gel filtration were concentrated and dialyzed against Tris-HCl buffer (30 mM trishydroxyaminomethane, pH 8.0) overnight, 500 μl of the obtained sample was fractionated by FPLC-Mono Q anion exchange chromatography (Pharmacia). The FPLC-Mono Q column (HR5/5) was equilibrated with, added the sample thereto, eluted with 3 ml of Tris-HCl buffer at a flow rate of 1 ml/minute, and then eluted with a linear gradient of 0–1 M sodium chloride 10 ml for 10 minutes. Each one-ml fraction was collected and dialyzed against phosphate-buffered saline solution (pH 7.4) overnight, and then assayed for the activity with rat bone marrow cells. As illustrated in FIG. 2, the immunosuppressive activity was detected in the fractions eluted with 0.55–0.75 M sodium chloride. The obtained samples are referred to as "partially purified sample".

Figure 3:
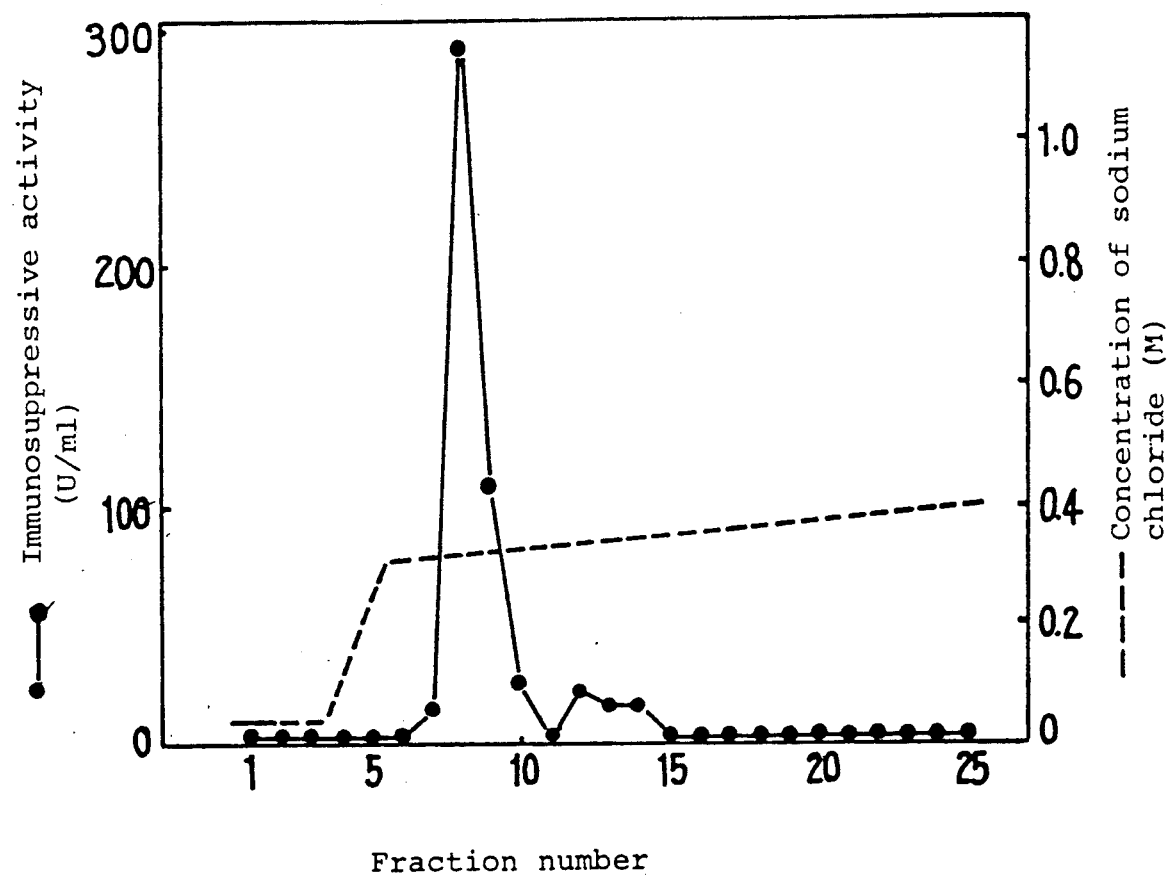
FIG. 3 shows the elution pattern in anion exchange chromatography using the FPLC-Mono Q column with a linear gradient of 0.3 to 0.5 M sodium chloride.

The active fraction of immunosuppressive factor of the present invention obtained from FPLC-Mono Q anion exchange chromatography was concentrated by ultrafiltration, dialyzed against Tris-HCl buffer (30 mM trishydroxyaminomethane, pH 8.0) overnight and further fractionated by FPLC-Mono Q anion exchange chromatography. The FPLC-Mono Q column was eluted with a linear gradient of 0.3–0.5 M sodium chloride 40 ml for 40 minutes. Each one-ml fraction was collected had dialyzed against phosphate-buffered saline solution (pH 7.4) overnight and then assayed for the activity with rat bone marrow cells. As shown in FIG. 3, the immunosuppressive activity was detected in fractions eluted with 0.31–0.32 M sodium chloride. The specific activity of the immunosuppressive factor of the present invention was about $10^6$ μ/ml, and this factor was purified to about 5800-fold from the culture supernatants with the recovery in activity of about 30%. This sample is referred to as "highly purified sample".

EXAMPLE 3

Highly purified sample of the immunosuppressive factor obtained by Example 2 was mixed with Tris-HCl buffer (40 mM trishydroxyaminomethane, pH 6.8) containing 4% sodium dodecyl sulfate (SDS), 4% 2-mercaptoethanol and 50% glycerin at a rate of 3:1 and heated at 90° C. for 3 minutes. Then SDSpolyacrylamide slab gel (2 mm×11 cm×14 cm) containing 10% polyacrylamide was prepared with gel forming apparatus (Atto, AE 6200 and AE 6210-gel forming apparatus) according to the method of Laemmli et al. described in Nature, vol. 227, p. 680, 1970. About 600 μl of the sample was applied on the top of the slab gel and electrophoresis was carried out at a constant current of 20 mA. After the electrophoresis, the gel was sliced into 2 mm-sections and each section was immersed into 1.0 ml of phosphate-buffered saline solution (pH 7.4) to extract at 4° C for 24 hours. After extraction, each extract was recovered with Pasteur pippette and rinsed with phosphate-buffered saline solution (pH 7.4) to obtain 2.5 ml of the extract. The activity of the immunosuppressive factor of the present invention was detected at the stained band of molecular weight of about 31,000 daltons in the extracted fractions.

Figure 4:
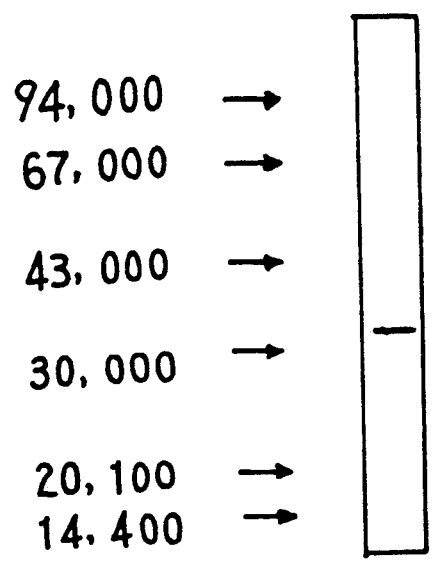
FIG. 4 shows the migration pattern of a purified sample of the immunosuppressive factor of the present invention in SDS-polyacrylamide gel electrophoresis.

Four times of preparative SDS-polyacrylamide gel electrophoresis were performed to recover the immunosuppressive factor of the present invention as a single band as shown in FIG. 4, and then the immunosuppressive factor fraction was deionized with ultrafiltration membrane (YM-10, Amicon) to provide as samples for the amino acid analysis.

The sample was subjected to hydrolysis with 6 N hydrochloric acid containing 4% thioglycolic acid at 110° C. for 22 hours, under reduced pressure. The amino acid composition (mol %) was analyzed with a high speed amino acid analyzer (Hitachi Model 835). The results are shown in Table 1.

TABLE 1

| Amino Acid Composition | Contents (mol %) |
| --- | --- |
| Asparagine inclusive of Aspartic acid | 9.6 |
| Threonine | 4.7 |
| Serine | 8.5 |
| Glutamine inclusive of Glutamic acid | 13.1 |
| Glycine | 16.9 |
| Alanine | 10.4 |
| Valine | 5.2 |
| Methionine | 1.1 |
| Isoleucine | 3.5 |
| Leucine | 7.3 |
| Tyrosine | 2.3 |
| Phenylalanine | 4.2 |
| Lysine | 5.8 |
| Histidine | 2.2 |
| Arginine | 3.7 |
| Proline | 2.3 |
| ½-Cystine | <1 |
| Tryptophan | <1 |

From the above facts, it is proven that the immunosuppressive factor of the present invention is the proteinic factor having a molecular weight of 45,000–65,000 and 150,000–200,000 by gel filtration, and about 31,000 daltons by SDS-polyacrylamide gel electrophoresis. These results suggested that the immunosuppressive factor might be existed as a homodimer or associated.

EXAMPLE 4

Figure 5:
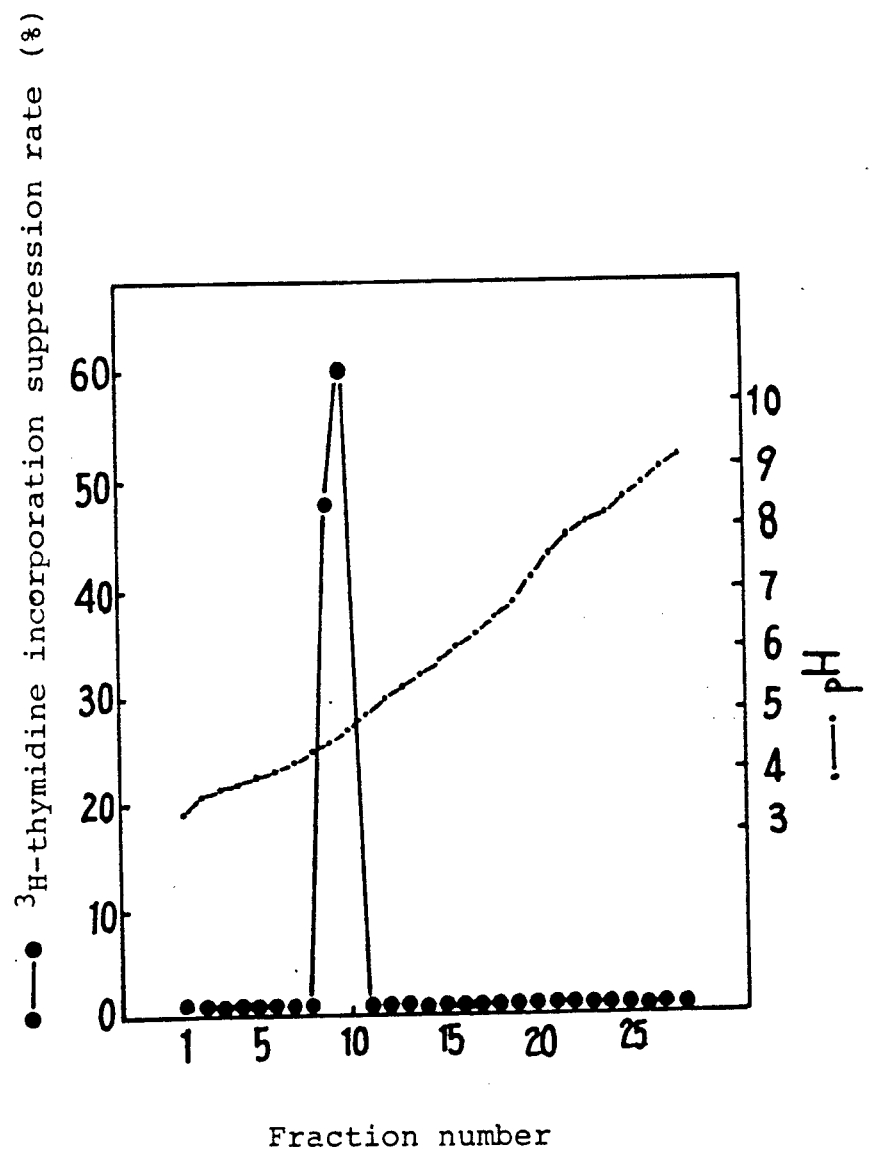
FIG. 5 shows the migration pattern of a concentrated culture supernatant containing the immunosuppressive factor of the present invention in preparative isoelectric focusing.

After dialysis against deionized water, the concentrated culture supernatants obtained by Example 2 was mixed with 4 g of Ultrodex (LKB), 5 ml of Ampholine (pH 3.5–10, LKB) and deionized water to obtain about 100 ml of gel. The gel was subjected to isoelectric focusing at a constant power of 18 W for 6–8 hours at 4° C. Immediately after the isoelectric focusing, the gel was sliced into 30 sections and pH value of each fractions was measured. Then, protein was eluted with deionized water from the gel. Each fraction was dialyzed against phosphate-buffered saline solution (pH 7.4) and assayed for the activity with rat bone marrow cells. As shown in FIG. 5, the activity was detected at a pH range of 4.6–4.8.

Partially purified immunosuppressive factor obtained by Example 2 was dialyzed against bis-Tris-iminodiacetic acid buffer [5 mM 2,2-bis(hydroxymethyl)-2,2',2''-nitrilotriethanol, pH 7.T]overnight and was fractionated by chromatofocusing using FPLC-Mono P column. As the starting buffer, 25 mM bis-Tris-iminodiacetic acid buffer (pH 7.1) was used and as the eluting buffer an aqueous iminodiacetic acid solution (pH 4.0) containing 10% Polybuffer 74 (Pharmacia) was used.

Figure 6:
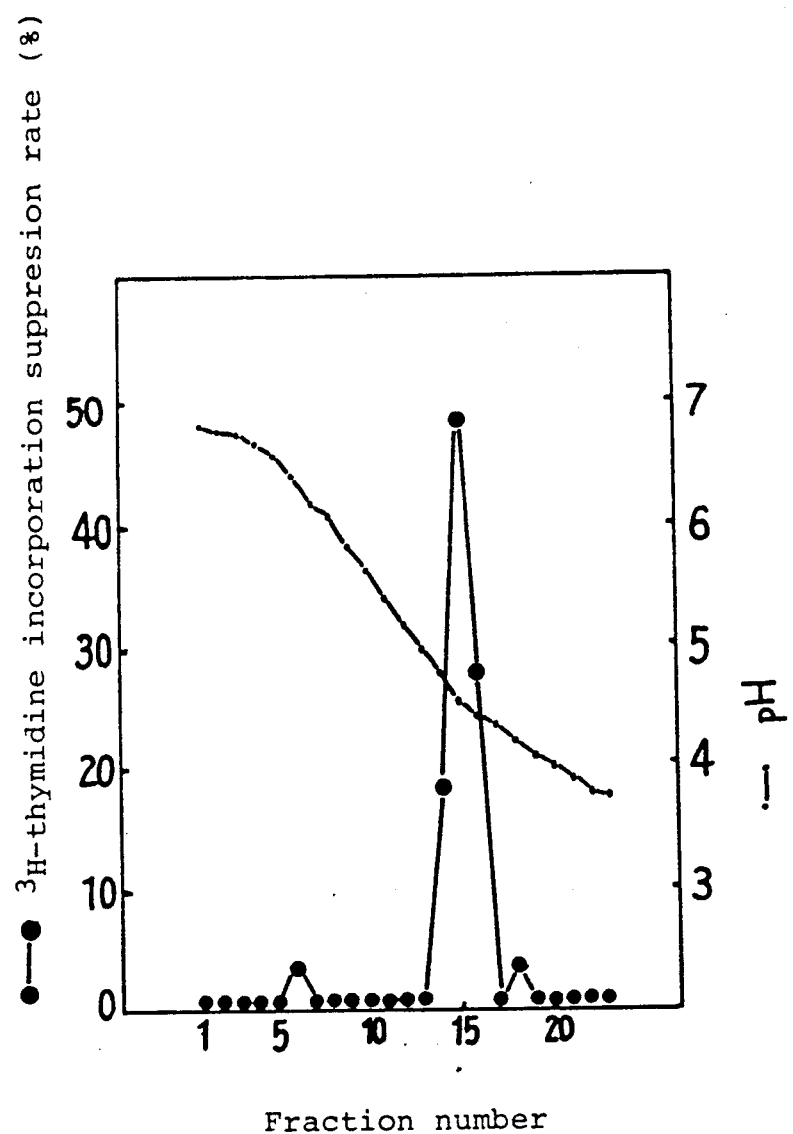
FIG. 6 shows the elution pattern of a purified sample of the immunosuppressive factor of the present invention in chromatofocusing using the FPLC-Mono P column.

The elution was carried out at a flow rate of 1 ml/minute for 45 minutes to obtain each two-ml fraction. After measuring the pH value, each of fraction was dialyzed against phosphate-buffered saline solution (pH 7.4) overnight and assayed for the activity with rat bone marrow cells. The activity of the immunosuppressive factor of the present invention was detected at a pH range of 4.6 to 4.8 as shown in FIG. 6. These results were coincident with the results of the isoelectric focusing.

EXAMPLE 5

Figure 7:
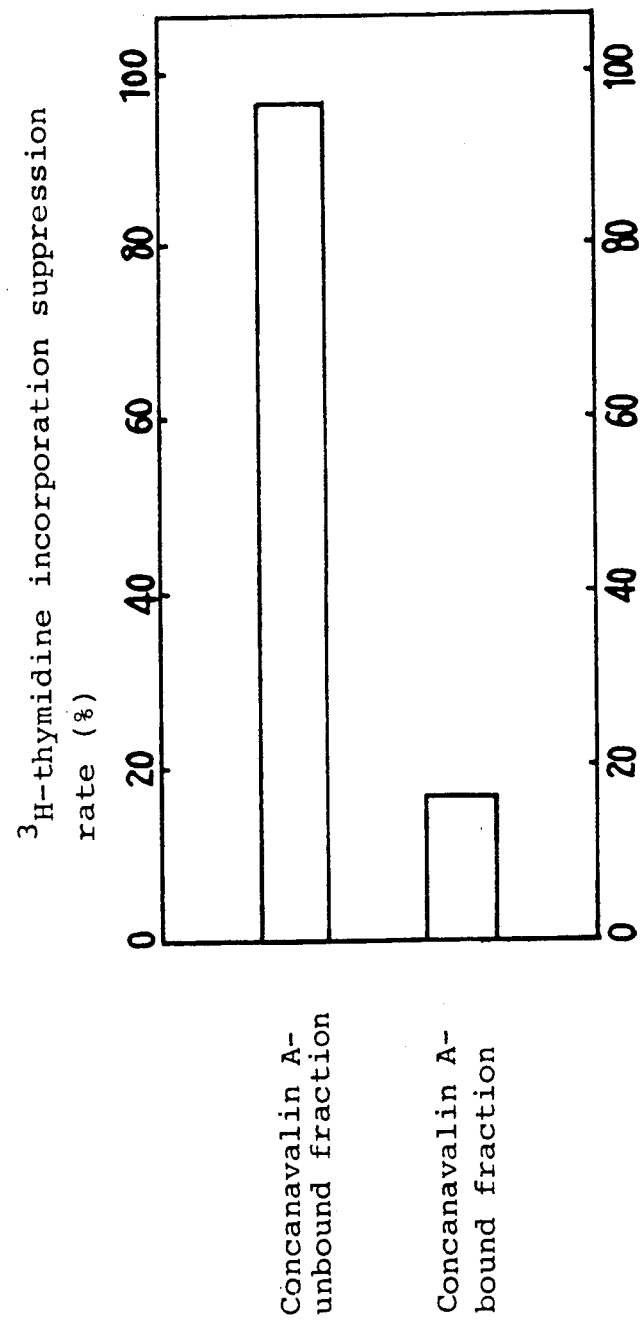
FIG. 7 shows the results of immobilized concanavalin A Sepharose affinity chromatography.

Partially purified immunosuppressive factor obtained by Example 2 was subjected to affinity chromatography with a immobilized concanavalin A-Sepharose 4B column (Pharmacia, 1.4×5 cm) and eluted with 50 ml of phosphate-buffered saline solution (pH 7.4) to obtain concanavalin A-Sepharoseunbound fraction. Then, concanavalin A-Sepharose-bound fraction was eluted with 50 ml of phosphate-buffered saline solution (pH 7.4) containing 0.2 M α-methyl-D-mannoside. Each fraction was dialyzed against phosphate-buffered saline solution overnight and assayed for the activity with rat bone marrow cells. As illustrated in FIG. 7, the immunosuppressive activity was detected in concanavalin A-Sepharose-unbound fractions.

Figure 8:
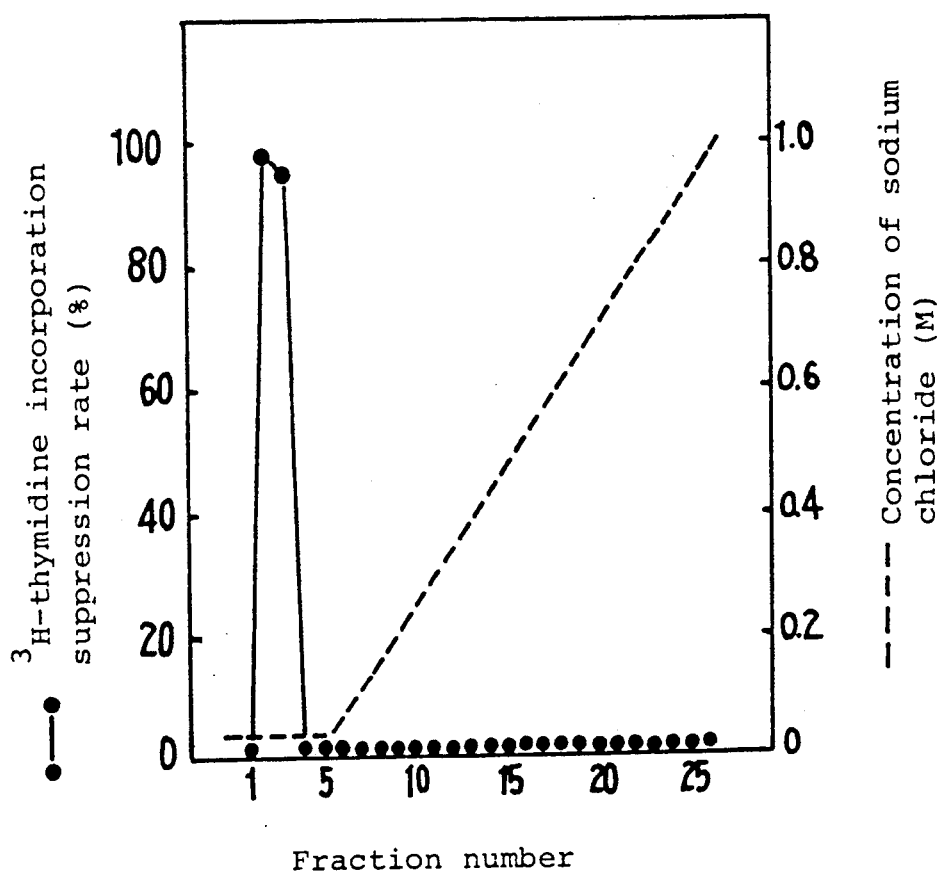
FIG. 8 shows the elution pattern in affinity chromatography using blue Sepharose CL6B.

The concentrated culture supernatants obtained by Example 2 were subjected to affinity chromatography with a blue Sepharose CL6B column (Pharmacia 1.4×10 cm). The blue Sepharose CL6B column was previously equilibrated with TrisHCl buffer (30 mM trishydroxyaminomethane, pH 8). After the addition of sample, 25 ml of blue Sepharose-unbound fractions were eluted with Tris-HCl buffer (pH 8). Then, the column was eluted with a linear gradient of 0 to 1 M sodium chloride. Each five-ml fraction was dialyzed against phosphate-buffered saline solution (pH 7.4) overnight and assayed for the activity with rat bone marrow cells. As shown in Figure 8, the immunosuppressive activity was detected in blue Sepharose-unbound fractions.

EXAMPLE 6

Partially purified immunosuppressive factor obtained by Example 2 was studied the stability to deoxyribonuclease I (DNase I), ribonuclease A (RNase A), trypsin, α-chymotrypsin, pronase, papain and periodic acid treatment, heat and pH. The immunosuppressive factor of the present invention with DNase I, RNase A, trypsin, α-chymotripsin, pronase or papain (Sigma) at a concentration of 50 μg/ml or 200 μg/ml was incubated at 37° C. for 3 hours and assayed for the activity with rat bone marrow cells. The periodic acid treatment was carried out by adding 5 mM sodium metaperiodate (Wako Pure Chemicals), keeping the reaction mixture for 3 hours in darkness under cooling, terminating the reaction with the addition of 5% weight/volume sucrose, and then standing for 30 minutes. After dialysis against phosphate-buffered saline solution (pH 7.4) overnight, the samples were assayed for the activity with rat bone marrow cells.

Figure 9:
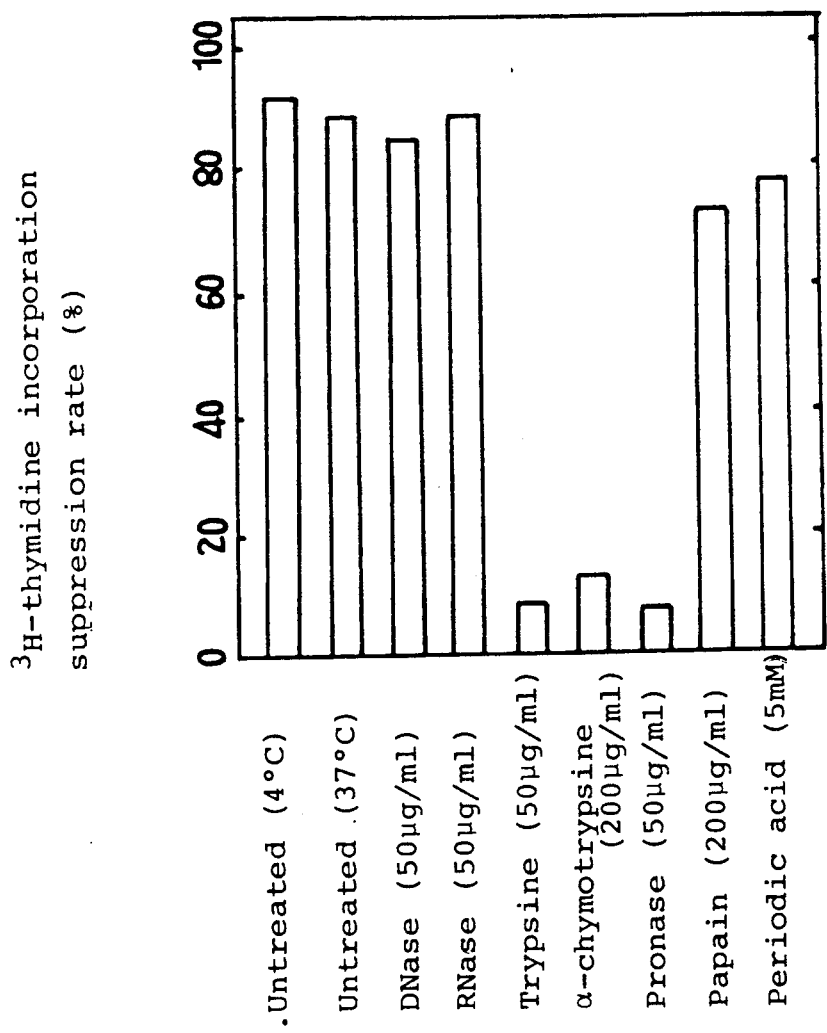
FIG. 9 shows the sensitivity of the immunosuppressive factor of the present invention to various enzymes and periodic acid.

As shown in FIG. 9, the immunosuppressive factor of the present invention was not sensitive to the treatment with DNase I, RNase A, papain and periodic acid, but was sensitive to 50 μg/ml of trypsin, 200 μg/ml of α-chymotrypsin, and 50 μg/ml of pronase.

The immunosuppressive factor of the present invention was stable at a pH range between 2 and 10, and was partially inactivated by heating at 56° C. and 90° C. for 30 minutes.

EXAMPLE 7

The immunosuppressive factor of the present invention was assayed for the activity with rat bone marrow cells by adding $10^{-4}$ M 2-mercaptoethanol, 5 μg/ml of levamisole, 50 mM N-acetyl-D-glucosamine, 50 mM N-acetyl-D-galactosamine, 50 mM α-methyl-D-mannoside, 10 mM L-arginine, or 10 mM L-ornithine. As a result of this experiment, the activity of the immunosuppressive factor was not inhibited by any agents.

Thus the immunosuppressive factor of the present invention was distinguishable from the known human immunosuppressive factor, SIRS factor, activity of which was blocked by 2-mercaptoethanol or levamisole, SISS-T factor, activity of which was blocked by N-acetyl-D-glucosamine, N-acetyl-D-galactosamine or α-methyl-D-mannoside, or arginase, activity of which was blocked by L-arginine or L-ornithine.

Partially purified immunosuppressive factor of the present invention did not show any cytotoxic activity against mouse L929 cells which were sensitive to lymphotoxin and tumor necrosis factor. In addition, the factor did not show anti-viral activity, growth-promoting activity against interleukin 2-dependent T cell lines and growth promoting and colony formation stimulating activity against bone marrow cells.

These results indicate that the immunosuppressive factor of the present invention is a novel immunosuppressant which is distinct from any other lymphokine described previously.

The following experiments illustrate the biological activity of the immunosuppressive factor of the present invention. The "SEM" used in the following experiments indicates standard error of the mean.

Experiment 1: Inhibitory effect on mitogen-induced IgM production from human peripheral blood lymphocytes Human peripheral blood lymphocytes obtained by the density gradient centrifugation were suspended at $5 \times 10^6$ cells/ml in RPMI 1640 medium supplemented with 10% heat-inactivated fetal calf serum, and pokeweed mitogen (PWM, 1/100 dilution) or Staphylococcus aureus Cowan I (SAC, 0.003%) was added thereto. The cell suspension (100 μl) was mixed with 100 μl of the test samples containing 50 U/ml of the immunosuppressive factor of the present invention in 96-well flat-bottomed microtiter plates. After incubation at 37° C. for 7 days under an atmosphere of 5% $CO_2$ in air, the supernatants were harvested and assayed for immunoglobulin M (IgM) concentration by enzyme-linked immunosorbent assay (ELISA). The results are shown in Table 1 as percent suppression compared with all amount of IgM in the absence of samples.

TABLE 1

| Mitogen | Immunosuppressive Factor (U/ml) | IgM Production (ng/ml ± SEM) | Suppression (%) |
|---|---|---|---|
| None | 0 | 60 ± 2 | — |
| PWM | 0 | 2670 ± 109 | 0 |
| PWM | 50 | 357 ± 61 | 86.6 |
| SAC | 0 | 2071 ± 76 | 0 |
| SAC | 50 | 157 ± 1 | 92.4 |

Experiment 2 : Inhibitory effect on spontaneous IgG production from human peripheral blood lymphocytes Human peripheral blood lymphocytes were suspended at $5 \times 10^6$ cells/ml in RPMI 1640 medium supplemented with 10% heat-inactivated fetal calf serum and 100 μl of the cell suspension was mixed with 100 μl of the test sample containing the immunosuppressive factor of the present invention in 96-well flat-bottomed microtiter plates. After culturing in the absence of stimulants at 37° C. for 7 days under an atmosphere of 5% $CO_2$ in air, the supernatants were harvested and assayed for immunoglobulin G (IgG) concentration by the ELISA method. Table 2 shows the results as percent suppression compared with an amount of IgG in the absence of test sample.

TABLE 2

| Immunosuppressive Factor (U/ml) | Spontaneous IgG Production (ng/ml ± SEM) | Suppression (%) |
|---|---|---|
| 0 | 287 ± 7 | — |
| 25 | 187 ± 52 | 34.8 |
| 50 | 101 ± 53 | 64.8 |

It is apparent from the results shown in Table 2 that the immunosuppressive factor of the present invention inhibits the spontaneous IgG production from human peripheral blood lymphocytes in a dose-dependent manner as compared in the absence of test sample.

Experiment 3 : Inhibitory effect on immunoglobulin production from human B lymphoblastoid cell lines Utilizing human B lymphoblastoid cell lines such as CCRF-SB and RPMI 8226 which were confirmed to produce IgG, and RPMI 1788 which was confirmed to produce IgM, the effect of the immunosuppressive factor of the present invention on these immunoglobulin productions was studied. All cells were suspended at $1 \times 10^5$ cells/ml in RPMI 1640 medium supplemented with 10% heat-inactivated fetal calf serum and 100 μl of the cell suspension was mixed with 100 μl of the test sample containing the immunosuppressive factor of the present invention in 96-well flat-bottomed microtiter plates. After culturing at 37° C. for 72 hours under an atmosphere of 5% $CO_2$ in air, IgG or IgM contents in the supernatants were determined by the ELISA method. The results are shown in Table 3. The numbers in parenthesis in Table 3 indicate percent inhibition as compared with IgG or IgM amounts in the absence of test samples.

TABLE 3

| Immunosuppressive Factor (U/ml) | Human B Lymphoblastoid Cell Lines | | |
|---|---|---|---|
| | CCRF-SB(IgG) (ng/ml ± SEM) | RPMI 8226(IgG) (ng/ml ± SEM) | RPMI 1788(IgM) (ng/ml ± SEM) |
| 0 | 271 ± 6 | 225 ± 6 | 165 ± 11 |
| 6.25 | 187 ± 10 (40.0) | 14 ± 1 (93.8) | 131 ± 19 (20.0) |
| 12.5 | 107 ± 4 (60.5) | 12 ± 2 (94.7) | 94 ± 13 (43.0) |
| 25 | 21 ± 1 (92.3) | 10 ± 1 (95.6) | 65 ± 6 (60.6) |

As shown in Table 3, the immunosuppressive factor of the present invention inhibited IgG production from CCRF-SB and RPMI 8226 and IgM production from RPMI 1788 in a dose-dependent manner as compared in the absence of the test sample.

Experiment 4 : Inhibitory effect on mouse allogenic mixed lymphocytes reaction (MLR)

Effect of the immunosuppressive factor of the present invention on mouse allogenic MLR was examined by mixing equal number of BALB/c mice ($H-2^d$)-derived splenocytes as responder cells and C57BL/6 mice-derived splenocytes which treated with mitomycin C as stimulator cells.

The responder cells were prepared according to the following procedure: The spleen was excised from 5 to 6 weeksaged male BALB/c mice and its splenocytes were suspended in RPMI 1640 medium supplemented with 5% heat-inactivated fetal calf serum, 60 μg/ml kanamycin sulfate, 2 mM L-glutamine, 10 mM N-2-hydroxyethylpiperazine-N'-2-ethanesulfonic acid and 0.1% sodium hydrogencarbonate. After lysis of red blood cells, the obtained single cell suspension of the splenocytes were resuspended at $10^7$ cells/ml in RPMI 1640 medium supplemented with $10^{-4}$ M 2-mercaptoethanol and 20% heat-inactivated fetal calf serum and used as responder cell suspensions.

The stimulator cells were prepared as follows: The spleen was excised from 5 to 6 weeks-aged male C57BL/6 mice and its splenocytes were suspended in RPMI 1640 medium. After lysis of the red blood cells, the obtained single cell suspension of splenocytes were treated with 40 μg/ml mitomycin C at 37° C. for 60 minutes, washed three times, and resuspended at $10^7$ cells/ml in RPMI 1640 medium supplemented with $10^{-4}$ M 2-mercaptoethanol and 20% heat-inactivated fetal calf serum to use as stimulator cell suspensions.

50 μl portions of responder cell suspension and stimulator cell suspension prepared as above were mixed with 100 μl of the test sample containing the immunosuppressive factor of the present invention in 96-well flat-bottomed microtiter plates, and cultured at 37° C. for 4 days under an atmosphere of 5% $CO_2$ in air.

After the culture, the cells were added with 0.5 μCi/well of 3H-thymidine and incubated for an additional 4 hours, and then collected with a cell harvester. Radioactivity incorporated into the cells was determined by a liquid scintillation counter and regarded as an index of lymphocytes blastogenesis induced by mouse allogenic MLR. The inhibitory effect of the immunosuppressive factor of the present invention on mouse allogenic MLR was estimated by calculating present suppression according to the following formula:

$$\text{Suppression (\%)} = \left(1 - \frac{cpm \text{ of } MLR \text{ in the presence of test sample} - cpm \text{ of responder alone}}{cpm \text{ of } MLR \text{ in the absence of test sample} - cpm \text{ of responder alone}}\right) \times 100$$

The results are summarized in Table 4.

TABLE 4

| Responder Cells | Stimulator Cells | Immunosuppressive Factor (U/ml) | $^3$H-thymidine Incorporation (cpm ± SEM) | Suppression (%) |
| --- | --- | --- | --- | --- |
| BALB/c | — | — | 3740 ± 965 | — |
| — | C57BL/6 | — | 768 ± 366 | — |
| BALB/c | C57BL/6 | — | 34926 ± 3090 | — |
| BALB/c | C57BL/6 | 500 | 5157 ± 846 | 95.5 |
| BALB/c | C57BL/6 | 250 | 8110 ± 84 | 86.0 |
| BALB/c | C57BL/6 | 125 | 9824 ± 407 | 80.5 |

Table 4 shows apparently that mouse allogenic MLR-induced lymphocytes proliferation is inhibited dose-dependently by the immunosuppressive factor of the present invention.

Experiment 5 : Inhibitory effect on mitogen-induced proliferation of human peripheral blood lymphocytes (1) Effect on concanavalin A-induced proliferation of human peripheral blood lymphocytes was examined by the following procedure: human peripheral blood lymphocytes obtained by the density gradient centrifugation were suspended at $5 \times 10^6$ cells/ml in RPMI 1640 medium supplemented with 10% heat-inactivated fetal calf serum, to which concanavarin A was added. The cell suspension (100 μl) was mixed with 100 μl of the test samples containing the immunosuppressive factor of the present invention in 96-well flat-bottomed microtiter plates. The number of human peripheral blood lymphocytes was $5 \times 10^5$ cells/well. After incubation at 37° C. for 72 hours under an atmosphere of 5% $CO_2$ in air, the cells were added with 3H-thymidine (0.5 μCi/well) and cultured for an additional 4 hours. At the termination of the culture, the cells were collected with a cell harvester. Radioactivity incorporated into the cells was determined by a liquid scintillation counter and regarded as an index of human peripheral blood lymphocytes proliferation. The results are shown in Table 5.

TABLE 5

| Samples | Dose (U/ml) | $^3$H-thymidine Incorporation (cpm ± SEM) | Suppression (%) |
| --- | --- | --- | --- |
| None | — | 1636 ± 522 | — |
| Con A alone | — | 26175 ± 4868 | — |
| Immuno-suppressive Factor | 50 | 350 ± 14 | 98.7 |
| | 25 | 1364 ± 205 | 94.8 |
| | 12.5 | 2078 ± 297 | 92.1 |

From the results shown in Table 5, the immunosuppressive factor of the present invention inhibited more than 90% of concanavalin A (Con A)-induced $^3$H-thymidine incorportion into human peripheral blood lymphocytes as compared in the absence of test sample.

(2) Effect on PWM- or SAC-induced proliferation of human peripheral blood lymphocytes was tested according to the following procedure: to human peripheral blood lymphocytes suspension prepared as above Experiment 5 (1), pokeweed mitogen (PWM, 1/100 dilution) or Staphylococcus aureus Cowan I (SAC, 0.003%) was added and 100 μl portions of these cell suspensions were mixed with 100 μl of the test samples containing the immunosuppressive factor of the present invention in 96-well flat-bottomed microtiter plates. The cells were cultured at 37° C. for 48 hours or 96 hours under an atmosphere of 5% $CO_2$ in air, and 0.5 μCi/well of $^3$H-thymidine was added and then incubated for an additional 4 hours. At the completion of the culture, the cells were collected with a cell harvester. Radioactivity incorporated into the cells was determined by a liquid scintillation counter and regarded as an index of human peripheral blood lymphocytes proliferation. The results are summarized in Table 6.

TABLE 6

| Culture time | Mitogen | Immuno-suppressive Factor (U/ml) | $^3$H-thymidine Incorporation (cpm ± SEM) | Suppression (%) |
| --- | --- | --- | --- | --- |
| 48 hours | — | 0 | 1917 ± 271 | — |
| | PWM | 0 | 5662 ± 327 | 0 |
| | PWM | 50 | 2110 ± 260 | 62.7 |
| | SAC | 0 | 7413 ± 88 | 0 |
| | SAC | 50 | 2074 ± 70 | 72.0 |
| 96 hours | — | 0 | 2793 ± 672 | — |
| | PWM | 0 | 10836 ± 425 | 0 |
| | PWM | 50 | 1871 ± 26 | 82.7 |
| | SAC | 0 | 12833 ± 332 | 0 |
| | SAC | 50 | 1239 ± 104 | 90.3 |

Experiment 6 : Inhibitory effect on colony-stimulating factor (CSF)-induced $^3$H-thymidine incorporation into mouse bone marrow cells and those colony formation (1) Effect on CSF-induced $^3$H-thymidine incorporation into mouse bone marrow cells was examined by the following procedure.

Bone marrow cells were collected from femurs of 8 to 12 weeks-aged male C3H/HeN mice and suspended at $2.5 \times 10^6$ cells/ml in RPMI 1640 medium containing 10% heat-inactivated fetal calf serum and added 10 or 100 U/ml mouse granulocyte macrophage-colony-stimulating factor (GM-CSF, Genzyme Co.) to suspension. The cell suspension (100 μl) was mixed with 100 μl of the test sample containing 50 U/ml of the immunosuppressive factor of the present invention in 96-well flat-bottomed microtiter plates. The number of mouse bone marrow cells was $2.5 \times 10^5$ cells/well. After culturing at 37° C for 16 or 39 hours under an atmosphere of 5% $CO_2$ in air, 0.5 μCi/well of $^3$H-thymidine was added and incubated for an additional 4 hours. After the completion of the incubation, the cells were collected with a cell harvester. Radioactivity incorporated into the cells was determined by a liquid scintillation counter. The results are summarized in Table 7, where the numbers in parenthesis indicate percent suppression.

TABLE 7

| Culture time | Immunosuppressive Factor (U/ml) | $^3$H-thymidine Incorporation (cpm ± SEM) | | |
|---|---|---|---|---|
| | | CSF 0 U/ml | CSF 10 U/ml | CSF 100 U/ml |
| 16 hours | 0 | 4219 ± 345 | 7465 ± 131 | 7332 ± 17 |
| | 50 | 1307 ± 110 (69.0) | 1860 ± 433 (75.1) | 1527 ± 55 (79.2) |
| 39 hours | 0 | 812 ± 71 | 2304 ± 593 | 7554 ± 584 |
| | 50 | 699 ± 114 (13.9) | 1008 ± 125 (56.3) | 1344 ± 534 (82.2) |

From these results shown in Table 7, it is obvious that the immunosuppressive factor of the present invention was inhibitory for not only $^3$H-thymidine incorporation in the absence of colony-stimulating factor (CSF) but also that in the presence of 10 or 100 U/ml of colony-stimulating factor (CSF).

(2) Effect on colony-stimulating factor (CSF)-induced colony formation of mouse bone marrow cells was examined according to the following procedure.

Mouse bone marrow cells were prepared from femurs of 8 to 12 weeks-aged male C3H/HeN mice were suspended at $1 \times 10^5$ cells/ml/35 mm plastic dish in MEM-2 medium containing 0.88% methyl cellulose, 20% horse serum, 5% mouse L cell-cultured supernatant as a sample of colony-stimulating factor (CSF), 20 U/ml of the immunosuppressive factor of the present invention. The cells were cultured at 37° C. for 7 days under an atmosphere of 5% $CO_2$ in air. Then the number of colony formed in each well was counted, and the results are shown in Table 8.

TABLE 8

| Immunosuppressive Factor (U/ml) | Number of Colony Formation (colony Number/$10^5$ cells) | Suppression (%) |
|---|---|---|
| 0 | 87 ± 4 | — |
| 20 | 23 ± 1 | 73.6 |

The results in Table 8 indicate that colony stimulating factor (CSF)-induced colony formation of mouse bone marrow cells was remarkably inhibited by the immunosuppressive factor of the present invention.

Experiment 7 : Inhibitory effect on interleukin 2 (IL-2) induced $^3$H-thymidine incorporation into IL-2-dependent mouse cell line (CTLL-2)

IL-2-dependent mouse cell line, CTLL-2, was suspended at $1 \times 10^5$ cells/ml in RPMI 1640 medium containing 10% heat-inactivated fetal calf serum and added 2.7 U/ml of the recombinant human interleukin 2 (r-hIL 2) to the suspension. 100 µl portions of the cell suspension was added to each well of 96-well flat-bottomed microtiter plates to which was added 100 µl of the test sample containing the immunosuppressive factor of the present invention. After incubation at 37° C. for 20 hours under an atmosphere of 5% $CO_2$ in air, to the cells were added 0.5 µCi/well of $^3$H-thymidine and the cells were cultured for an additional 4 hours, then collected by using a cell harvester. Radioactivity incorporated into the cells was determined by a liquid scintillation counter and the results are shown in Table 9.

TABLE 9

| IL 2 (U/ml) | Immunosuppressive Factor (U/ml) | $^3$H-thymidine Incorporation (cpm ± SEM) | Suppression (%) |
|---|---|---|---|
| 0 | 0 | 716 ± 77 | — |
| 2.7 | 0 | 23269 ± 769 | 0 |
| 2.7 | 25 | 11117 ± 554 | 52.2 |
| 2.7 | 50 | 9394 ± 565 | 59.6 |
| 2.7 | 100 | 3246 ± 1079 | 86.1 |
| 2.7 | 200 | 2806 ± 623 | 81.9 |

It is apparent from Table 9 that the immunosuppressive factor of the present invention inhibited $^3$H-thymidine incorporation into CTLL-2 cells treated with 2.7 U/ml of IL-2.

Experiment 8 : Inhibitory effect on lymphotoxin (LT) production from human B lymphoblastoid cell line, RPMI 1788

100 µl portions of RPMI 1788 cell suspension prepared at $1 \times 10^5$ cells/ml in 10% heat-inactivated fetal calf serumcontaining RPMI 1640 medium were mixed with 100 µl of test sample which contained the immunosuppressive factor of the present invention in 96-well flat-bottomed microtiter plates. After incubation at 37° C. for 72 hours under an atmosphere of 5% $CO_2$ in air, the supernatants were assayed for the cytotoxic activity against mouse L929 cells as an index of LT production. The results are shown in Table 10.

TABLE 10

| Immunosuppressive Factor (U/ml) | LT Production (U/ml) | Suppression (%) |
|---|---|---|
| 0 | 235 | — |
| 6.25 | 130 | 44.7 |
| 12.5 | 107 | 54.5 |
| 25 | 90 | 61.7 |

From the results in Table 10, it is noted that the immunosuppressive factor of the present invention inhibited LT production from RPMI 1788 cells dose-dependently.

Experiment 9 : Inhibitory effect on growth of various cultured tumor cells

Various hemopoietic cell-derived cultured tumor cells such as CCRF-CEM, CCRF-HSB-2, MOLT-4, U937, K562, HL-60, Raji and Daudi, were suspended at $2 \times 10^5$ cells/ml in RPMI 1640 medium containing 10% fetal calf serum. 50 µl of these cell suspensions was mixed with 50 µl of the test sample containing 50 U/ml of the immunosuppressive factor of the present invention in 96-well flat-bottomed microtiter plates. After incubation at 37° C. for 72 hours under an atmosphere of 5% C02 in air, 10 µl of 3-(4,5-dimethylthiazol-2-yl)-2,5-diphenyltetrazolium bromide (MTT, 5mg/ml), which had been described in J. Immunol. Methods, vol. 65, p. 55, 1983, to form a blue-coloured formazan product by the mitochondorial enzyme succinate-dehydrogenase in viable cells, was added to each well. After formazan crystals were formed by the incubation at 37° C for 4 hours under an atmosphere of 5% CO₂ in air, 100 μl of 0.01 N hydrochloric acid solution containing 10% sodium dodecyl sulfate was added to dissolve the crystals, then the plates were incubated at 37° C. overnight. At the completion of the incubation, 100 μl of the supernatant of each well was transfered to the microtest plates for the measurement of absorbance and the optical density of each well was measured using a spectrophotometer for microplate with a wavelength of 550 nm and a reference wavelength of 660 nm. The growth inhibitory activity against each cultured tumor cell was expressed at percent growth inhibition in Table 11 by calculating with the following formula; Growth inhibition (%)=

Growth inhibition (%) =

$$\left(1 - \frac{\text{absorbance in the presence of a test sample}}{\text{absorbance in the absence of the sample}}\right) \times 100$$

TABLE 11

| Cultured Tumor Cells | Absorbance in the Absence of Immuno-suppressive Factor | Absorbance in the Presence of Immuno-suppressive Factor | Suppression (%) |
|---|---|---|---|
| CCRF-CEM | 506 ± 4 | 333 ± 7 | 34.2 |
| CCRF-HSB-2 | 249 ± 4 | 147 ± 9 | 41.0 |
| MOLT-4 | 535 ± 4 | 438 ± 18 | 18.1 |
| U937 | 575 ± 6 | 259 ± 5 | 54.9 |
| K562 | 435 ± 3 | 362 ± 9 | 16.8 |
| HL-60 | 649 ± 11 | 386 ± 1 | 40.5 |
| Raji | 362 ± 1 | 100 ± 1 | 72.4 |
| Daudi | 687 ± 10 | 915 ± 11 | 71.2 |

These data in Table 11 indicate that the immunosuppressive factor of the present invention inhibited the growth of various hemopoietic cells (including lymphoid cells)-derived cultured tumor cells.

Experiment 10 : Inhibitory effect on growth and antibody productivity of human B lymphoblastoid cell line, CCRF-SB Time course of the inhibitory activity caused by the immunosuppressive factor of the present invention was analysed with CCRF-SB cells in the effects on its growth and antibody production. The immunosuppressive factor of the present invention (25 U/ml) was added to CCRF-SB cell suspension. The cell growth and antibody production after incubation for 24, 48 or 72 hours were measured by colorimetric assay with MTT and the ELISA method, respectively. The results are shown in Table 12.

TABLE 12

| Culture Time | Suppression of Cell Growth (%) | Suppression of Antibody Production (%) |
|---|---|---|
| 24 hours | 25.9 | 0 |
| 48 hours | 44.3 | 93.0 |
| 72 hours | 83.4 | 96.0 |

The data in Table 12 apparently indicate that the immunosuppressive factor of the present invention caused only a weak growth inhibition of about 26% and did not show any inhibitory effect on antibody production in the 24-hour culture whereas both cell growth and antibody production were markedly inhibited in the 72-hour culture, i.e. 83% and 96%, respectively. These results, therefore, suggest that the immunosuppressive factor of the present invention showed immunosuppressive activity rather due to inhibition of cell proliferation than cytolytic effect which was recognized as the action of cytotoxic factors such as to more necrosis factor and lymphotoxin.

As described above, the novel immunosuppressive factor of the present invention possesses potent immunosuppressive activities and are useful for a therapuetic drug or reagent.

The present invention has been fully explained in the description and examples given above, but any variations and modifications thereof may be made without departing from the spirit and scope of the present invention.

We claim:
1. A substantially purified human immunosuppressive factor derived from human T cell leukemia cells and characterized by having the following properties (1)-(12):
   (1) molecular weight: 45,000 to 65,000 daltons and 150,000 to 200,000 daltons by gel filtration, and approximately 31,000 daltons by SDS-polyacrylamide gel electrophoresis;
   (2) isoelectric point: 4.6 to 4.8;
   (3) being elutable at a concentration of 0.31 to 0.32 M sodium chloride by FPLC-Mono Q anion exchange chromatography;
   (4) not adsorbable to immobilized concanavalin A Sepharose or blue Sepharose;
   (5) resistant to deoxyribonuclease, ribonuclease, papain and periodic acid but sensitive to trypsin, α-chymotrypsin or pronase;
   (6) stable at pH 2 to 10;
   (7) stable for a long time at 4° C. but partially inactivated by heat treatment at 56° C. or 90° C. for 30 minutes;
   (8) not inhibitable by 2-mercaptoethanol, levamisole, N-acetyl-D-glucosamine, N-acetyl-D-galactosamine, α-methyl-D-mannoside, L-arginine or L-ornithine;
   (9) suppressing production of antibody;
   (10) suppressing blastogenesis of lymphocytes;
   (11) suppressing cell proliferation; and
   (12) having structural amino acids whose contents (mol %) are asparagine (including aspartic acid), 9.0 mol %; theonine, 4.7 mol %; serine, 8.5 mol %; glutamine (including glutamic acid), 13.1 mol %; glycine, 16.9 mol %; alanine, 10.4 mol %; valine, 5.2 mol %; methionine, 1.1 mol %; isoleucine, 3.5 mol %; leucine, 7.3 mol %; tyrosine, 2.3 mol %; phenylalanie, 4.2 mol %; lysine, 5.8 mol %; histidine, 2.2 mol %; arginine, 3.7 mol %; proline, 2.3 mol %; ½ cystine, <1 mol %; and tryptophan, <1 mol %.

* * * * *